(12) United States Patent
Nag et al.

(10) Patent No.: US 6,624,197 B1
(45) Date of Patent: Sep. 23, 2003

(54) DIPHENYLETHYLENE COMPOUNDS

(75) Inventors: Bishwajit Nag, Fremont, CA (US); Satyanarayana Medicherla, Cupertino, CA (US); Debendranath Dey, Fremont, CA (US)

(73) Assignee: Calyx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/642,618

(22) Filed: Aug. 17, 2000

Related U.S. Application Data

(63) Continuation-in-part of application No. 09/074,925, filed on May 8, 1998, now Pat. No. 6,245,814.

(51) Int. Cl.⁷ ............................................. A61K 31/19
(52) U.S. Cl. ...................... 514/570; 514/717; 514/720; 514/730; 514/733; 514/764
(58) Field of Search ................. 514/570, 717, 514/720, 733, 730, 764

(56) References Cited

U.S. PATENT DOCUMENTS

| | | |
|---|---|---|
| 3,275,520 A | 9/1966 | Strobel et al. |
| 3,609,183 A | 9/1971 | DeWald et al. |
| 3,683,009 A | 8/1972 | Middleton |
| 4,217,366 A | 8/1980 | Kikumoto et al. |
| 4,271,186 A | 6/1981 | Forster et al. |
| 4,284,637 A | 8/1981 | Kikumoto et al. |
| 4,310,534 A | 1/1982 | Kikumoto et al. |
| 4,312,855 A | 1/1982 | Grand |
| 4,326,055 A | 4/1982 | Loeliger |
| 4,716,905 A | 1/1988 | Schmued |
| 4,866,086 A | 9/1989 | Boyle et al. |
| 4,929,635 A | 5/1990 | Coquelet et al. |
| 4,940,707 A | 7/1990 | Klaus et al. |
| 5,087,637 A | 2/1992 | Janssen et al. |
| 5,162,337 A | 11/1992 | Elbrecht et al. |
| 5,171,753 A | 12/1992 | Munson, Jr. et al. |
| 5,189,056 A | 2/1993 | Orlando et al. |
| 5,246,936 A | 9/1993 | Treacy et al. |
| 5,250,562 A | 10/1993 | Klaus et al. |
| 5,314,693 A | 5/1994 | Suga |
| 5,378,705 A | 1/1995 | Klaus et al. |
| 5,409,953 A | 4/1995 | Pettit et al. |
| 5,430,062 A | 7/1995 | Cushman et al. |
| 5,457,226 A | 10/1995 | Gygax |
| 5,494,932 A | 2/1996 | Cardin et al. |
| 5,521,160 A | 5/1996 | Chucholowski et al. |
| 5,525,632 A | 6/1996 | Obsumi et al. |
| 5,532,129 A | 7/1996 | Heller |
| 5,559,151 A | 9/1996 | Adorante et al. |
| 5,565,191 A | 10/1996 | Raspanti |
| 5,565,322 A | 10/1996 | Heller |
| 5,569,786 A | 10/1996 | Pettit et al. |
| 5,583,128 A | 12/1996 | Bhatnagar |
| 5,587,150 A | 12/1996 | Deflandre et al. |
| 5,589,506 A | 12/1996 | Hashimoto et al. |
| 5,672,625 A | 9/1997 | Cardin et al. |
| 5,674,906 A | 10/1997 | Hatanaka et al. |
| 5,705,530 A | 1/1998 | Adorante et al. |
| 5,716,928 A | 2/1998 | Benet et al. |
| 5,731,353 A | 3/1998 | Ohsumi et al. |
| 5,733,909 A | 3/1998 | Black et al. |
| 5,767,268 A | 6/1998 | Chucholowski et al. |
| 5,770,620 A | 6/1998 | Mjalli et al. |
| 5,827,898 A | 10/1998 | Khandwala et al. |
| 6,245,814 B1 * | 6/2001 | Nag et al. |

OTHER PUBLICATIONS

Cas Onlin Printout; Spaeth (Beilstein 3150042; Spaeth; Kromp, Chem. Ber., Coden: CHBeam, 74, 1941, 189,191).*

Pettit et al., "Isolation, Structure, Synthesis and Antimitotic Properties of Combretastains B–3 and B–4 from Combretum Caffrum", *Journal of Natural Products*, vol. 51, No. 3, (1988) pp. 517–527.

Green, R.H., "Syntheses of Differanisole A.," *Tetrahedron Lett.*, vol. 38, No. 26 (1997) pp. 4697–4700.

Reddy, K.L. et al., "From Styrenes to Enantiopure alpha–Arylglycines in Two Steps", *J. Am. Chem. Soc.*, vol. 120, No. 6 (1998) pp. 1207–1217.

Sheehan et al., "A Constituent of *Pterocarpus marsupium*, (–)–Epicatechin, as a Potential Antidiabetic Agent," Journal of Natural Products, vol. 46, No. 2 (1983) pp. 232–234.

He, et al., "Spectrometric Study of α–Phenylcinnamic Acids", *Chinese Chemical Letters*, vol. 8, No. 10 (1997) pp. 883–884.

Chakravarthy et al., "The Prophylactic Action of (–)–Epicatechin Against Alloxan Induced Diabetes in Rats", *Life Science*, vol. 29 (1981) pp. 2043–2047.

Farbooniay et al., "Antihyperlipidemic Effect of Flavonoids From *Pterocarpus marsupium*," Journal of Natural Products, vol. 60, No. 7 (1993) pp. 989–994.

Manickham et al., "Antihyperglycemic Activity of Phenolics from *Pterocarpus marsupium*," *Journal of Natural Products*, vol. 60, No. 6 (1997) pp. 609–610.

Maurya et al., "Constituents of *Pterocarpus marsupium*," *Journal of Natural Products*, vol. 47, No. 1 (1983) pp. 179–181.

Maurya et al., "Marsupsin, a New Benzofuranone from *Pterocarpus Marsupium* ROXB.," *Heterocycles*, vol. 19, No. 11 (1982) pp. 2103–2107.

* cited by examiner

*Primary Examiner*—Samuel Barts
(74) *Attorney, Agent, or Firm*—Pillsbury Winthrop LLP

(57) ABSTRACT

Novel diphenylethylene and styrenes are provided which are administered orally to decrease blood glucose levels in rats. The glucose tolerance in insulin resistant rats is also shown, as well as lowering of triglyceride levels in serum insulin resistant, hyperinsulinemic and hypertriglycedemic rats. The compounds are orally effective anti-diabetic agents that potentially may reduce abnormality of glucose and lipid metabolism in diabetes.

18 Claims, 6 Drawing Sheets

DIPHENYLETHYLENE COMPOUNDS

This is a continuation-in-part of Ser. No. 09/074,925, filed May 8, 1998 now U.S. Pat. No. 6,245,814, which is incorporated by reference in its entirety.

FIELD OF THE INVENTION

The field of the invention is novel diphenylethylene compounds and their use for treatment of diabetes.

BACKGROUND OF THE INVENTION

Extracts of the leaves, flowers, and gum of the tree *Pterocarpus marsupium* Roxb. (Leguminosae), also known as the Indian Kino Tree, have been used traditionally for the treatment of diarrhea, toothaches, fever and urinary and skin infections. Extracts of the bark have been long regarded as useful for the therapy of diabetes. Hypoglycemic activity of a naturally occurring pterostilbene, trans-1-(3,5-dimethoxyphenyl)-2-(4-hydroxyphenyl)-ethylene, isolated from the heartwood of pterocarpus marsupium as been reported by Manickam et al., *J. Nat. Prod.*, 1997, 60:609–610. However, this pterostilbene is water insoluble and has not been shown to be efficacious in the treatment of diabetes, particularly in instances where insulin is present but inactive. The cause of diabetes is yet unknown, although both genetics and environment appear to be factors.

Insulin dependent (Type I) and non-insulin dependent (Type II) are the types of diabetes. Type I is an autonomic immune disease in which the responsible autoantigen is still unknown. Patients of Type I need to take insulin intravenously to survive. However, Type II diabetes, the more common form of the disease, is a metabolic disorder resulting from the body's inability to make a sufficient amount of insulin or to properly use the insulin that is produced within the body. Insulin secretion and insulin resistance are considered the major defects, however, the precise genetic factors involved in the mechanism remain unknown.

Patients with diabetes usually have one or more of the following defects: less production of insulin by the pancreas; over secretion of glucose by the liver; impairment of glucose uptake by the skeletal muscle; defects in glucose transporters; desensitation of insulin receptors; and defects in the metabolic breakdown of polysaccharides. Other than the intravenous application of insulin, there are four classes of oral hypoglyceric agents in use.

| Class | Approved Drugs | Mechanisms of Action | Limitations |
|---|---|---|---|
| sulfur urea | 4 (1st generation) and 2 (2nd generation) | acts on pancreas to release more insulin | dev. of resistance |
| biguanides | metformin | reduces glucose secretion by liver; improves insulin sensitivity | liver problems, lactic acidosis |
| alpha-glucosidase inhibitor | acarbose | interferes with digestive process; reduces | only useful at post-pradiandio level |
| thiazolidine-dione | troglipzone | glucose absorption reduces insulin resistancy | "add-on" with insulin; not useful for people with heart and liver disease |

As is apparent from the above table, each of the current agents available for use and treatment of diabetes has certain disadvantages. Accordingly, there is a continuing interest in the identification and development of new agents, particularly, water soluble agents which can be orally administered, for the use of treatment of diabetes.

Besides the pterostilbene discussed above, (−)-epicatechin, has also been isolated from pterocarpus marsupium by Sheehan et al., *J. Nat. Prod.*, 1983, 46:232, and has been reported as having a hypoglycemic effect. See also Chakravarthy et al., *Life Sciences*, 1981, 29:2043–2047. Other phenolic type compounds have been isolated from pterocarpus marsupium by Maurya et al., *J. Nat. Prod.*, 1984, 47:179–181; Jahromi et al., *J. Nat. Prod.*, 1993, 56:989–994; and Maurya et al., *Heterocycles*, 1982, 19:2103–2107.

SUMMARY OF THE INVENTION

A class of novel diphenylethylenes is provided having the following formula I.

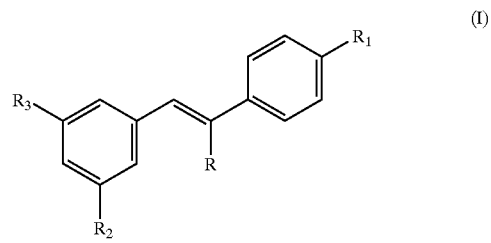

wherein R is hydrogen or —$CO_2Z$, Z is hydrogen or a cation;

and $R_1$, $R_2$ and $R_3$ are each independently H, —OH or —$OR_4$, wherein $R_4$ is linear or branched alkyl of 1–12 carbon atoms; with the proviso that when R is hydrogen and $R_2$=$R_3$=—OMe, then $R_1$ is not —OH. The configuration around the double bond may be E or Z.

A novel class of styrenes is also provided of the formula II

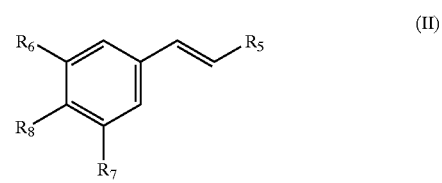

wherein $R_5$ is hydrogen or methyl; $R_6$ and $R_7$ are independently hydrogen or OMe; $R_8$ is hydrogen or hydroxy. The configuration around the double bond may be E or Z.

Pharmaceutical compositions of compounds of the formula I or II are provided for treatment of diabetes comprising of therapeutically effective amount of the compound in a physiologically acceptable carrier.

A method of treating diabetes is also provided comprising step of orally administering to a subject suffering from a diabetic condition a therapeutically effective amount of a compound of formula I or II.

DESCRIPTION OF THE PREFERRED EMBODIMENTS

Figure 1:
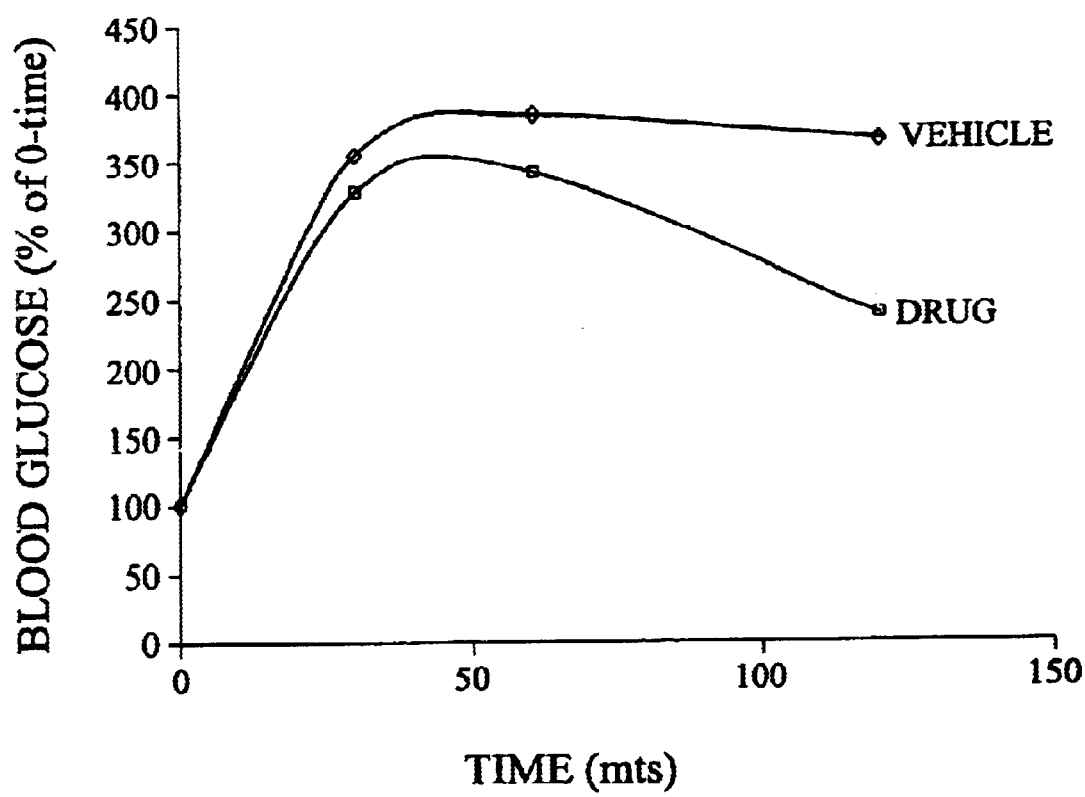
FIG. 1 shows the effect of administration of the compound in Example 1 on blood glucose level in STZ induced diabetic rats.

Diphenylethylene of the formula I and styrenes of formula II are provided by synthetic methods generally known in the art. Particularly, preferred are compounds of formula I in which $R_2$ and $R_3$ are methoxy. A particularly preferred species is a compound in which $R_2$ and $R_3$ are methoxy and R is $CO_2Z$, and $R_1$ is OH. The cations for Z are typically sodium, lithium, potassium, or any other physiologically acceptable cation which may be introduced orally to a subject.

Particularly preferred styrenes of the formula II are those in which $R_6$ and $R_7$ are methoxy and $R_8$ is hydrogen. Another preferred class of the formula II includes compounds wherein $R_6$ and $R_7$ are hydrogen and $R_8$ is hydroxy.

The compounds of the formula I and II are made by methods known in the art. In general, for the compounds of formula I, appropriate benzaldehyde and phenylacetic acid starting materials are condensed, then decarboxylated, if required.

SCHEME I

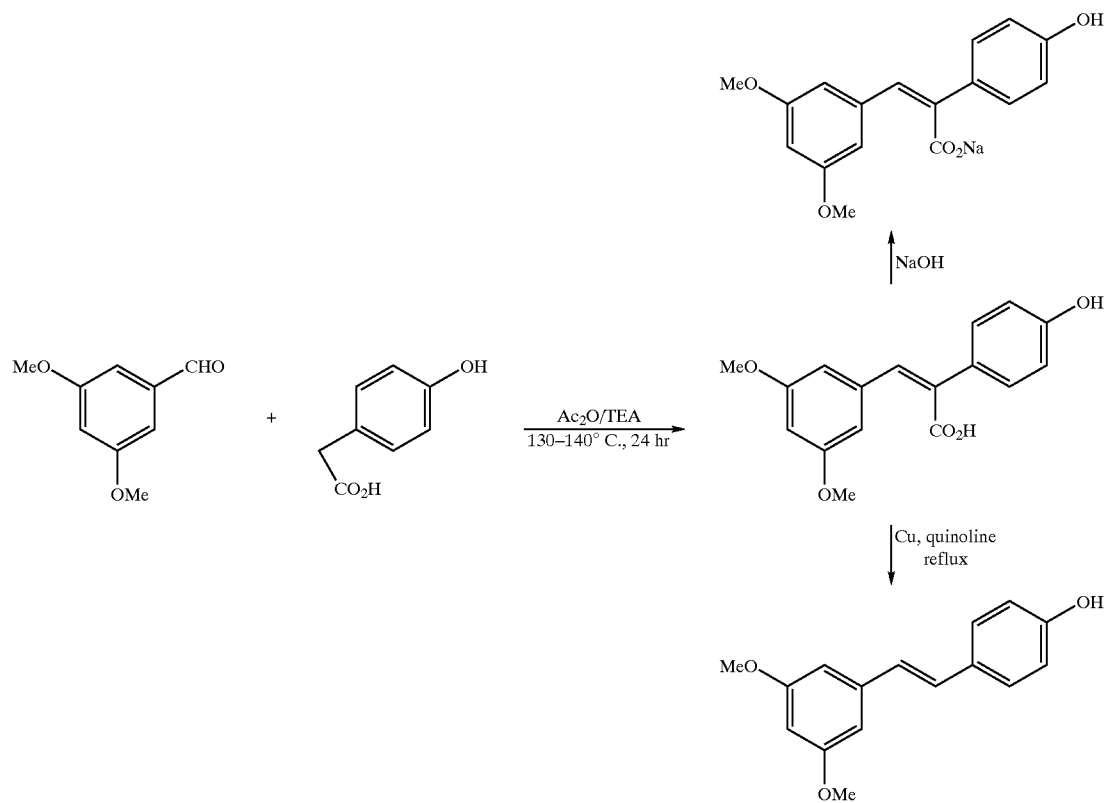

Compounds of the formula II are prepared generally from a benzaldehyde starting material and alkylidenetriphenylphosphorane by the Wittig reaction.

SCHEME II

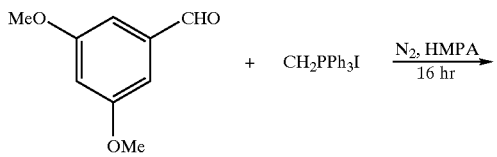

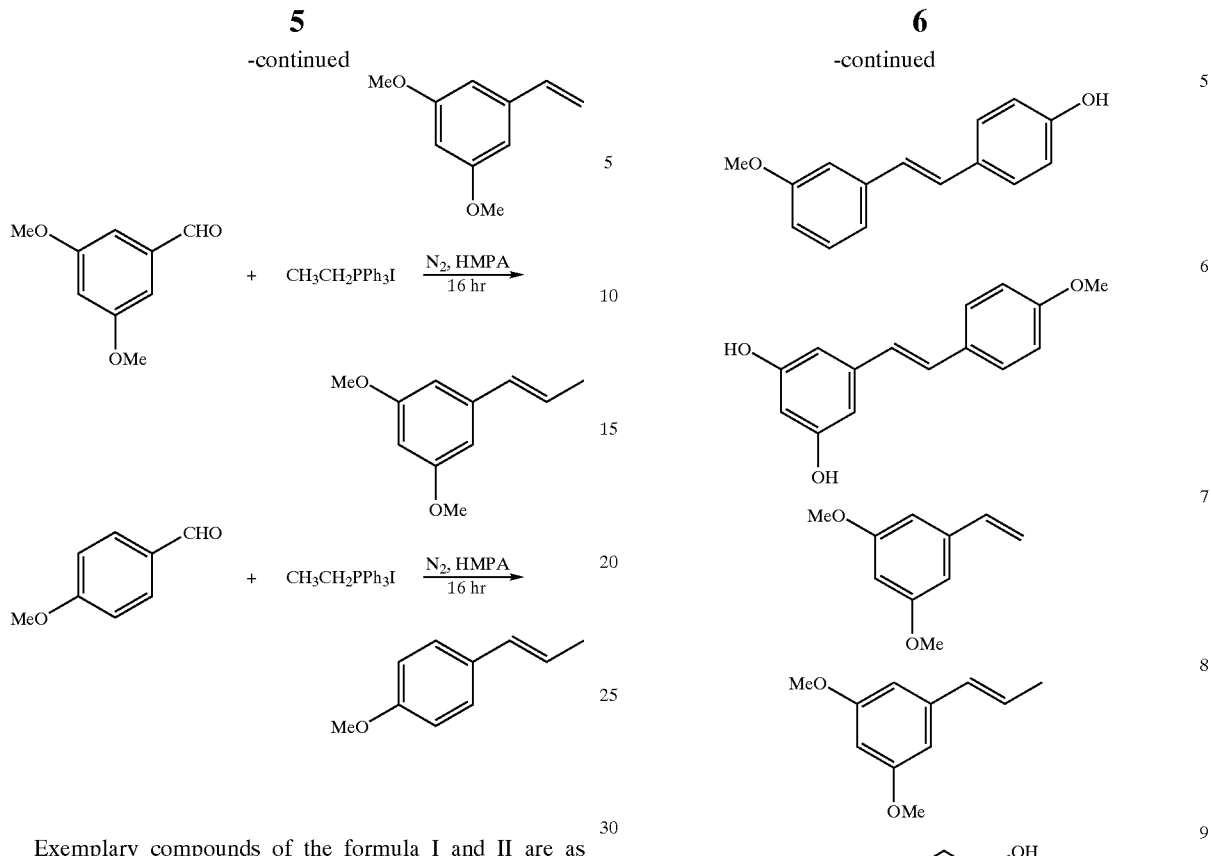

Exemplary compounds of the formula I and II are as follows:

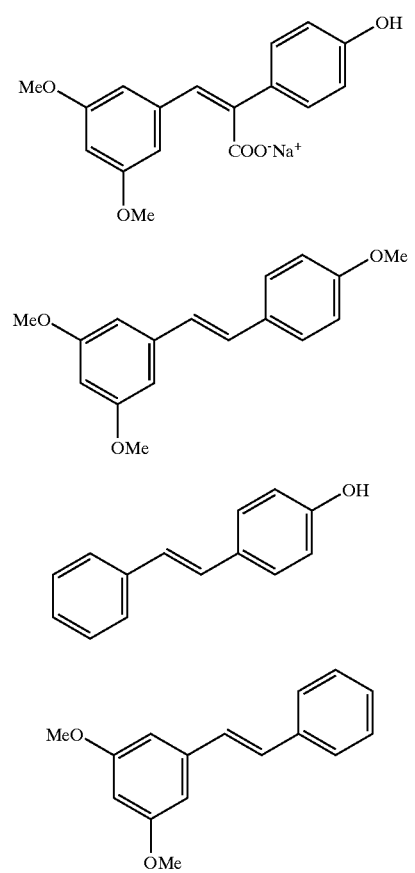

The compounds according to the present invention may be combined with a physiologically acceptable vehicle in pharmaceutical composition. The particularly preferred form of composition is an orally administered capsule or solution in which the compound is delivered in water, saline, a phosphate buffer, or lyophilized powder in a form of tablets or capsules which also includes various fillers and binders. The effective dosages of the compound in a composition will be selected by those of ordinary skill in the art and may empirically be determined.

The compounds of the present invention are useful for the treatment of diseases such as diabetes characterized by the presence of elevated blood glucose levels, that is, hyperglycemic disorders such as diabetes melitus, including both Type I and II diabetes as well as other hyperglycemic related disorders such as obesity, increased cholesterol, kidney related disorders, and the like.

By "treatment", it is meant that the compound is administered at least to reduce the blood glucose level in the patient suffering from the hyperglycemic disorder. The compound is administered in an amount sufficient to reduce blood glucose level to an acceptable range, wherein an acceptable range means ±10%, usually ±8% and usually ±5% of the normal average blood glucose level for the subject. A variety of subjects may be treated with the compounds to reduce blood glucose levels, such as livestock, valuable or rare animals, pets, as well as humans. The compounds may be administered to the subject suffering from the hyperglycemic disorder using a convenient administration technique, including intravenous, intradermal, intramuscular subcutaneous oral and the like. However, the oral route of administration is particularly preferred. The dosage delivered to the host will necessarily depend upon the route by which the compound is delivered, but generally ranges from 5 to 500 mg/70 kg human body weight or typically from about 50 to 200 mg/70 kg human body weight.

Of particular interest are methods of treating human hyperglycemic disorder such as diabetes, including both Type I and II, where the compound is administered to the human suffering from the hyperglycemic disorder to at least reduce the blood glucose level of the subject to about the normal blood glucose range for a human.

The following examples are offered by way of illustration and not intended to limit the invention in any way.

EXAMPLE 1

Preparation of Sodium 2-(4-Hydroxyphenyl)-3-(3,5-dimethoxyphenyl)-propenoate and Its Acid To a mixture of 3,5-dimethoxybenzaldehyde (30 mM) and p-hydroxyphenyl acetic acid (30 mM) was added 5 mL acetic anhydride and 2.5 mL of triethylamine (TEA). See Pettit et al. (1). After being stirred at 130–140° C. for 24 hr., the mixture was cooled to room temperature and quenched with 25 mL concentrated HCl and extracted with $CH_2Cl_2$. The organic extract was further extracted with 1N NaOH, then the NaOH extract was washed with water, the aqueous layer was acidified with concentrated HCl and washed with water to obtain the crude product. Crude product was recrystallized from ethanol/water to yield the E acid Ic.

To decarboxylate Ic, 1 g under $N_2$, 3 g of Cu powder and 30 mL of quinoline were refluxed, stirring for 4 hrs. The reaction mixture was filtered, diluted with water and extracted with $CH_2Cl_2$. The organic layer was dried and concentrated, and the decarboxylated product was purified by flash chromotography.

To convert the acid Ic or Id to the sodium salt Ib or Ia, respectively, to 1 g of Ic or Id NaOH solution was added under room temperature. The mixture was shaken and freeze dried to give acid salt.

The E-acid was again synthisized by a similar procedure. To a mixture of 3,5-dimethoxybenzaldehyde (5.0 g, 30 mmol) and p-hydroxyphenyl acetic acid (4.57 g, 30 mmol), acetic anhydide (10 ml) and triethylamine (4.2 ml, 30 mmol) were added under a nitrogen atmosphere, and the mixture was heated at 130–140° C. for 18 hours. The mixture was cooled to 20° C. Then concentrated Hcl (20 ml) was added to the reaction mixture slowly, keeping the temperature below 30° C. The precipitate obtained was filtered and dissolved in $CH_2Cl_2$. Methylene chloride solution was extracted with 2M aqueous NaOh solution. The alkaline layers were pooled together, washed with $CH_2Cl_2$ and acidified with concentrated Hcl. The aqueous layer thus obtained was acidified with concentrated HCl to a pH of 1. The solid separated was filtered and washed with cold water. Crude product was recrystallized from the +OH—$H_2O$ mixture to yield white crystals of Ic.

Four lots of the E-isomer prepared as described above were separated in 40 µl samples by HPLC on an Intersil ODS-3 (GL Sciences) column, 250×4.6 mm, and eluted with 62%v eluent A and 38%v eluent B. Eluent A is 0.1% formic acid in water; B is 0.1% formic acid in ACN. All samples showed a major amount of the E-isomer, with a minor amount of the Z-isomer at relative retention time 1.073±0.001. By this method, presence of the Z-isomer was estimated to be from 0.27% to 3.09% in these samples.

The Z-acid Id was synthesized by a procedure described by Kessar et al. (2), who showed that E-α-phenyl cinnamic acids can be converted to similar Z-α-phenyl cinnamic acide by prolonged heating under basic conditions. The E-acid Ic (1.2 g, 4.0 mmol) was dissolved in a mixture of triethylamine (5.0 ml) and acetic anhydride (0.5 ml) and heated to reflux for 24 hours. The mixture was then cooled, diluted with ethyl acetate, and extracted sequentially first with 5% Hcl (aqueous) then with 2 N NaOH and water. The combined basic aqueous solutions were acidified to a pH of 5 with acetic acid and cooled, and the solid was filtered. The filtrate was further acidified with concentrated Hcl. Precipitation occurred upon cooling. The solid was collected by filtration and washed with fresh water. The solid compound was air dried to yield Id.

Both isomers were subjected to NMR, pKa, HPLC, and UV spectral analysis.

E-Isomer. The free acid form of the E-isomer showed a chemical shift for the olefinic proton (in DMSO-d6) of 7.59. The olefinic proton shift for the E-isomer calculated with ChemDraw Software is 7.54 (see Formula Ic). The free acid has a melting point of 225–227° C. and a pKa of 6.2.

$^1$H NMR (DMSO-$d_6$) δ8 12.48 (br, 1H), 9.42 (br, 1H), 7.59 (s, 1H), 6.95 (d, J=8.6 Hz, 2H), 6.77 (d, J=8.6Hz, 2H), 6.35 (t, J=2.2 Hz, 1H), 6.27 (d, J=2.2Hz, 2H), and 3.55 (s, 6H).

Z-Isomer. The $^1$H NMR analysis of the Z-isomer produced as described above showed the chemical shift of the olefinic proton to be 6.81 as a free acid in DMSO-$d_6$. The calculated chemical shift of the olefinic proton of the Z-isomer from the ChemDraw Software is 7.31 (see Formula Id). These results confirm that the product produced was indeed the Z-isomer. The free acid form has a melting point of 135–137° C. and a pKa of 5.3.

Comparison of Isomers Produced.

The chemical shifts of the olefinic protons of the prepared E- and Z- isomers prepared as described above are 7.59 and 6.81, respectively. The calculated shifts for these compounds are 7.54 and 7.31, respectively; the compound with the higher chemical shift of the olefinic proton is the E-isomer.

The analysis of the Perkin reaction product of phenyl acetic and benzaldehyde (a similar compound), indicates that the pKa of the isomers of a-phenyl cinnamic acid are 6.1 for the e-isomer and 4.8 for the Z-isomer (3). Accordingly, between the two isomers, the one having the higher pKa is the E-isomer.

HPLC AND UV Spectral Analysis

The reverse-phase HPLC analysis of E- and Z-isomers was performed by a linear gradient using a 0.1% formic acid/water/acetonitrile system on a G.L. Sciences Intersil ODS-3 column (250×4.6 mm, 5 µm), monitored at 280 nm. In this system, the E- and Z-isomers were eluted at 17.4 and 17.9 min, respectively.

Each isomer has a distinct UV spectrum. The λmax values for the E-isomer are 227 nm and 284 nm, and those for the Z-isomer are 221 nm and 303 nm.

REFERENCES

1. Pettit G B, Singh S B, Schmidt J M, Niven M l, Hamel E, and Un C M. Isolation, structure, synthesis, and antimitotic properties of combretastatins B-3 and B-4 from Combretum caffrum. *J Nat Prod* 1988; 51:517–527.
2. Kessar S V, Nadir U K, Gupta Y P, Pahwa P S, and Singh P. Reactions of halogenated α-phenylcinnamic acids with potassium amide in liquid ammonia: Part I-Reactions of cis- & trans-2-chloro-α-phenylcinnamic acids. *Indian J Chemistry* 1981; 20B:1–3.

3. Fieser L F and Williamson K L. In Experiments in Organic Chemistry, Third Edition. Lexington MA: D.C. Heath and Company, 1955, p. 182.

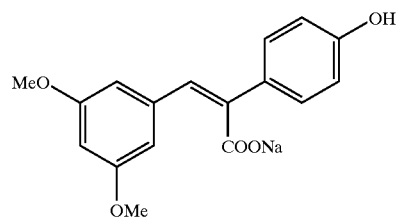

Ia(Z)

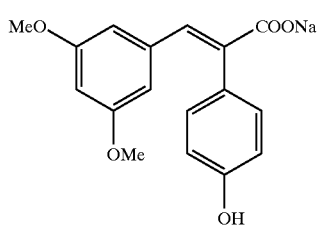

Ib(E)

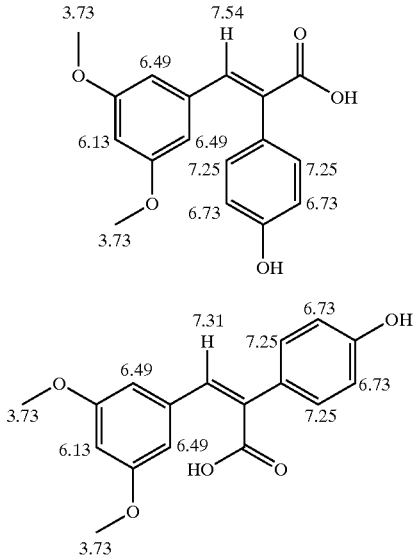

Ic(E)

Id(Z)

EXAMPLE 2

Figures 6A, 6B:
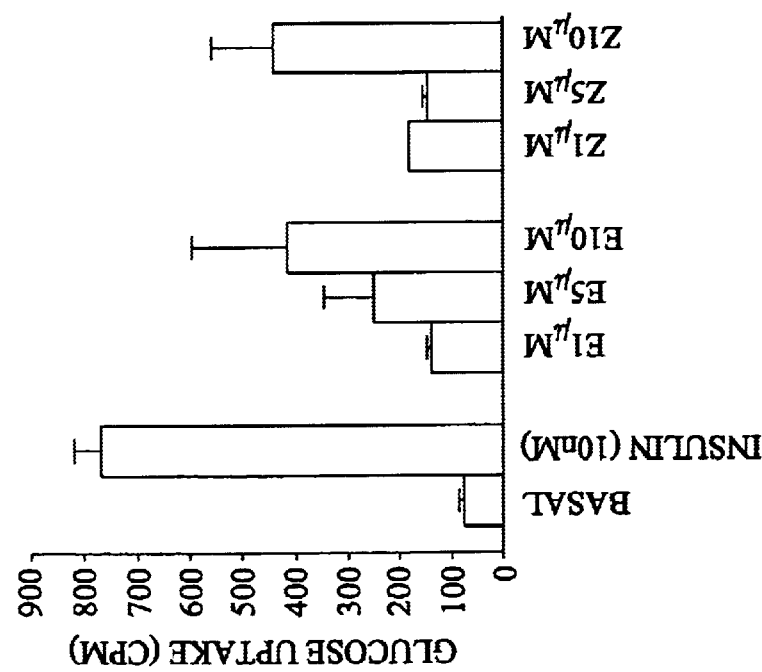
FIGS. 6A and 6B shows the data from Example 2.

In Vitro Assay. Both isomers of example 1 were capable of stimulating rapid glucose uptake in the glucose-uptake assay in rate adipocytes (see FIG. 6A). Similar to insulin, the glucose uptake in primary rate adipocytes was stimulated by the Z-isomer, and this glucose uptake was inhibited in the presence of the known P13 kinase inhibitor wortmannin (see FIG. 6B). Other studies have shown that the stimulatory effect of the E-isomer on primary adipocytes is additive to that of low doses of insulin. As FIG. 6B shows, a similar result was obtained with the Z-isomer. Based on these in-vitro results, we conclude that both isomers promote the rapid transport of glucose in primary adipocytes.

EXAMPLE 3

Serum samples from human subjects were tested for presence of the compounds in Example 1 after receiving doses of the preparation containing a mixture of the Z-isomer and E-isomer. This method was not capable of separating E- and Z-isomers and provided the information regarding the presence of total quantity of both the isomers. By HPLC:

The serum samples left after analysis were processed and reanalyzed by modified HPLC method. Different groups of human subjects had received three different does of 500, 1,000, and 2,000 mg/day. Blood samples were collected at 30 min, 1, 4, and 8 hours after dosing. The quantity of Z-isomer present in the serum at 4 and 8 hours was close to the lower limit of quantitation thus those results were not taken into account. Serum samples from four subjects at a dose level of 500 mg/day and 1,000 mg/day and two subjects from the 2000 mg/day group were analyzed and the result is summarized in the table below.

| Dose mg/day | Subject No. | At 30 min % of Z-Isomer | Average | At 60 min % of Z-Isomer | Average |
|---|---|---|---|---|---|
| 500 | 9 | 11.3 | 9.0% | 8.98 | 12.6% |
|  | 9 | 5.40 |  | 9.27 |  |
|  | 12 | 11.81 |  | 19.50 |  |
|  | 12 | 7.44 |  | 12.84 |  |
| 1000 | 16 | 5.02 | 7.4% | 5.81 | 9.0% |
|  | 16 | 8.77 |  | 8.89 |  |
|  | 18 | 5.85 |  | 9.02 |  |
|  | 18 | 9.85 |  | 12.34 |  |
| 2000 | 16 | 4.65 | 5.2% | 4.40 | 6.1% |
|  | 18 | 5.67 |  | 7.89 |  |

Materials and Methods

Processing of Samples

Dried extracts of blood PK samples representing 8 human subjects with 4 time points each of one or more of 3 dose levels, were prepared. Using liquid-liquid extraction with diethyl ether on 200 μl aliquots of either plasma sample or sample diluted to range with blank plasma; the recovered organic phase was dried at elevated temperature for approximately 15 minutes.

For chromatography with resolution of E and Z forms, a subset of thse samples (Subjects 9, 12, 16, and 18, for 4 sets of 500 mg/day dose, 4 sets of 1,000 mg, and 2 sets of 2,000 mg/day) was reconstituted in 100 μl of eluent and 40 °μl was analyzed with UV detection. The relative amounts of E and Z forms were determined. Z-isomer was present in all 0.5 hour samples, and decresed in amount through the 4 hour and 8 hour time points, just as did the E-isomer.

Materials and Methods

Beckman 126 Solvent Mod. (Instrument 1), 168 PDA Detector, 507e Autosampler

GL Sciences Intersil ODS-3, 250×4.6 mm, 5 μm (Analytical)

Isocratic Eluent: A=62%v (0.1% HCOOH in H2O), B=38%v (0.1% HCOOH in ACN)

Flow: 1.0 mL/min

Injection: 40 μL, micro pick-up mode

Detection: Diode array from 200 to 400 nm, and single channel UV at 280 and 320 nm.

Analysis of serum samples showed in vivo isomeriztion of the E- form to the Z- form.

EXAMPLE 4

An in vitro stability study was conducted for 24 hours at 37° C. in commerical rat serum to study the stability of E- and Z-isomers of the acids from Example 1. Serum was spiked to 20 μg/ml with compound then sub-aliquoted at different timepoints, from 0 through 24 hours, and incubated at $_{37}$° C. After incubating for the indicated time, samples were processed and analyzed by reverse phse HPLC.

Materials

Chemicals, reagents, and stock material:
  Water, HPLC grade, B&J AH3654, lot BV953. Opened container
  Acetonitrile, HPLC grade, B&J AH 015-4, lot BX949. Opened container
  Formic acid, 96%, Aldrich 25136-4, lot 03831. Opened container
  Acetone, ACS grade 99.5%, Aldrich 17912-4, lot AI 00147AI, Opened container Instruments, columns, and other materials:
  Balance, Sartorius BA110s, Ser #30803774; calib 10/11/99 w/ ISO 9001 seal.
  C-18 SPE columns, JT Baker Bakerbond 7020-1, 100 mg, lot M40550
  Vacuum manifold, Supelco Visiprep
  Beckman 126 Solvent Mod. (Instru 1), 507e Autosampler, 168 Photodiode
  GL Sciences Intersil ODS-3, 250×4.6 mm×5 μm, Ser # 9LI86024

Methods

Preparation of Stock Soln:

E-isomer stock was made up in water at 3.0 mg/mL, from 3.3 mg of dried compound. Z-isomer was prepared in a similar fashion.

Preparation of Serum Mode:

Serum was obtained by sacrifice from a male Sprague-Dawley rate. Rate serum was spiked to 20 μg/ml (0.02 μg/ml) with either E-isomer or Z-isomer from a 3.0 μg/μl stock soln, and 200 μl of spiked sample was sub-aliquoted for each of 9 perspective timepoints (0 hours through 24 hours). After incubation at 37° C. for the indicated time, a given sample was withdrawn and processed. Serum protein was precipitated with cold acetone, and duplicate 200 μl aliquots of supernatant were treated on 1 ml SPE columns and eluted with methanol. Collected eluate (500 μl, in excess) was dried under nitrogen gas, and reconstituted for chromatography in 200 μl of RP-HPLC eluent.

Preparation of Controls:

E- and Z-isomers non-serum controls at 0.02 μg/μl was prepared by diluting 3.0 μg/μl aqueous stock 150-fold (just as with the spiked serum), diluting with PBS buffer. These controls were prepared for SPE, just as with the spiked serum samples, except they were reconstituted in 200 μl (2×volume=0.5×concentration relative to samples). An aliquot of PBS diluent was processed by SPE, as a reagent control.

For a serum background control, 200 μL aliquots of serum ambient and at 37° C. for 6h were processed by acetone and SPE; each dried material was recon in 100 μL of eluent.

For a response and recovery control, the 0.02 μg/μL soln in PBS was directly assayed by HPLC at 0.8 μg inject. The 0.02 μg/μL response and recovery control was also incubated at 37° C. for 6h to access stability of compound in biologically buffered media at incubation temperature.

A queue control was placed at the start of the second day of chromatography; this was 0.02 μg/μL E-isomer in PBS, stored overnight at 4° C.

To source recovery losses, the SPE load flow-through of 4h spiked serum, and the source acetone supernatant (diluted 1:1 with eluent) were examined.

Chromatography:
  RP-HPLC: Isocratic Eluent: 40% B. A=0.1%v HCOOH, H20; B=0.1%v HCOOH, ACN. Flow=1 mL/min
  Detector: PDA; 320 and 280 nm
  Inject volume: 40 μL, μL pick-up mode Analysis of data suggested that purity of both E- and Z-isomers showed very minor change during 24 hour incubation at 37° C. This finding is different from the observation made for in vivo experiment Example 3 where in humans there was conversion of E-isomer into Z-isomer.

EXAMPLE 5

General Procedure for Preparation of Styrene Derivatives

General Procedure: To a stirred solution of Wittig salt (1 mM) in dry THF at −78° C. was added potassium (bistrimethylsilyl)amide (1 mM). After being stirred under $N_2$ for 2 hours at −78° C., HMPA (2 mM) and aldehyde (1 mM) in THF was added and stirred at room temperature for 16 hours. The reaction was quenched with water and extract with diethyl ether. Product was purified by flash chromatography.

EXAMPLE 6

Referring to FIG. 1, the streptozotocin (STZ)-induced diabetic rats were produced by injecting STZ (40 mg/kg/BW) intravenously. The blood glucose levels were measured 72 hrs. after the injection. Experiments were conducted with rats showing fasting blood glucose levels more than 200 mg/dl. The compound in example 1 was administered at a dose of 20 mg/kg/BW orally to test rats. Simultaneously, a control group received vehicle PBS (phosphate buffered saline). Soon after administration, glucose tolerance tests were conducted by administering glucose (2 g/kg/BW) and blood glucose levels were monitored at different time points. The results are shown in FIG. 1. Between 30 and 60 minutes after administration, the blood glucose levels in the rats receiving the test compound began to diminish.

EXAMPLE 7

Figure 2:
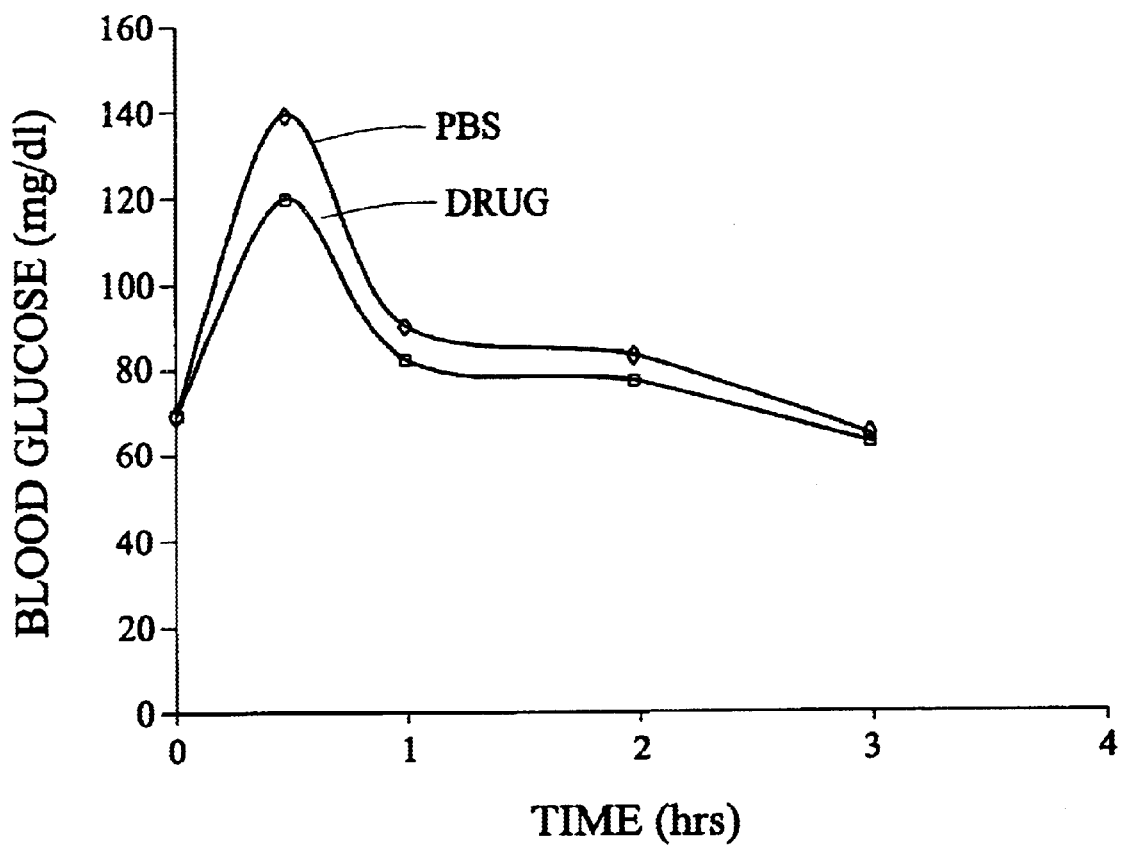
FIG. 2 shows the effect of the compound in Example 1 on glucose tolerance in hyperinsulinemic and insulin resistant Zucker rats.

Referring to FIG. 2, glucose tolerance was measured in Zucker (fa/fa) rats. Hyperinsulinemic and insulin resistant Zucker rats were randomized into two groups designated as a test group and a control group to check the effect of compound in Example 1 on glucose tolerance and insulin levels. Six of the test group rats were given dosages of the compound of Example 1 (20 mg/kg/BW/oral) once per day for period of three days. The control group was gavaged with an equal volume of PBS. An oral glucose (2 g/kg/BW) tolerance test was conducted on overnight-fasted rats soon after administration of test materials on day-3. Referring to FIG. 2, it shows that the compound of Example 1 improves glucose tolerance in insulin resistant obese Zucker rats.

EXAMPLE 8

Figure 3:
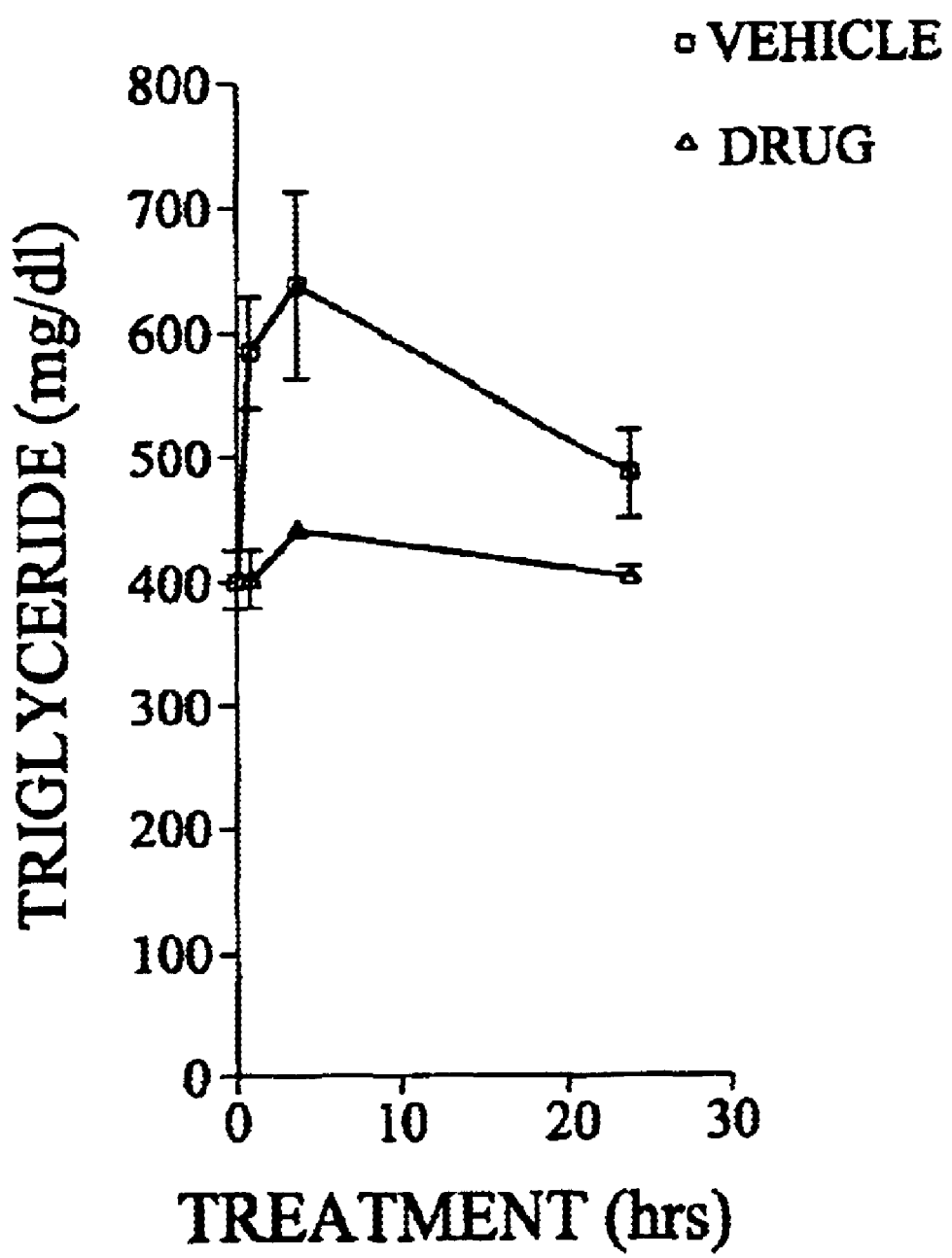
FIG. 3 shows the effect of the compound in Example 1 on plasma triglyceride levels in Zucker rats.

Referring to FIG. 3, twelve insulin resistant hyperinsulinemic obese Zucker (fa/fa) rats were randomized into two groups designated as a test group and a control group. Six of the test group rats received the compound of Example 1 (20 mg/kg/BW) at zero hour. The control group received an equal volume PBS. Plasma triglyceride levels were monitored for a period of 24 hours on fed state. The results are shown in FIG. 3. The compound from Example 1 lowers plasma triglyceride levels in obese insulin resistant hyperinsulinemic and triglyceridemic Zucker rats.

EXAMPLE 9

Figure 4:
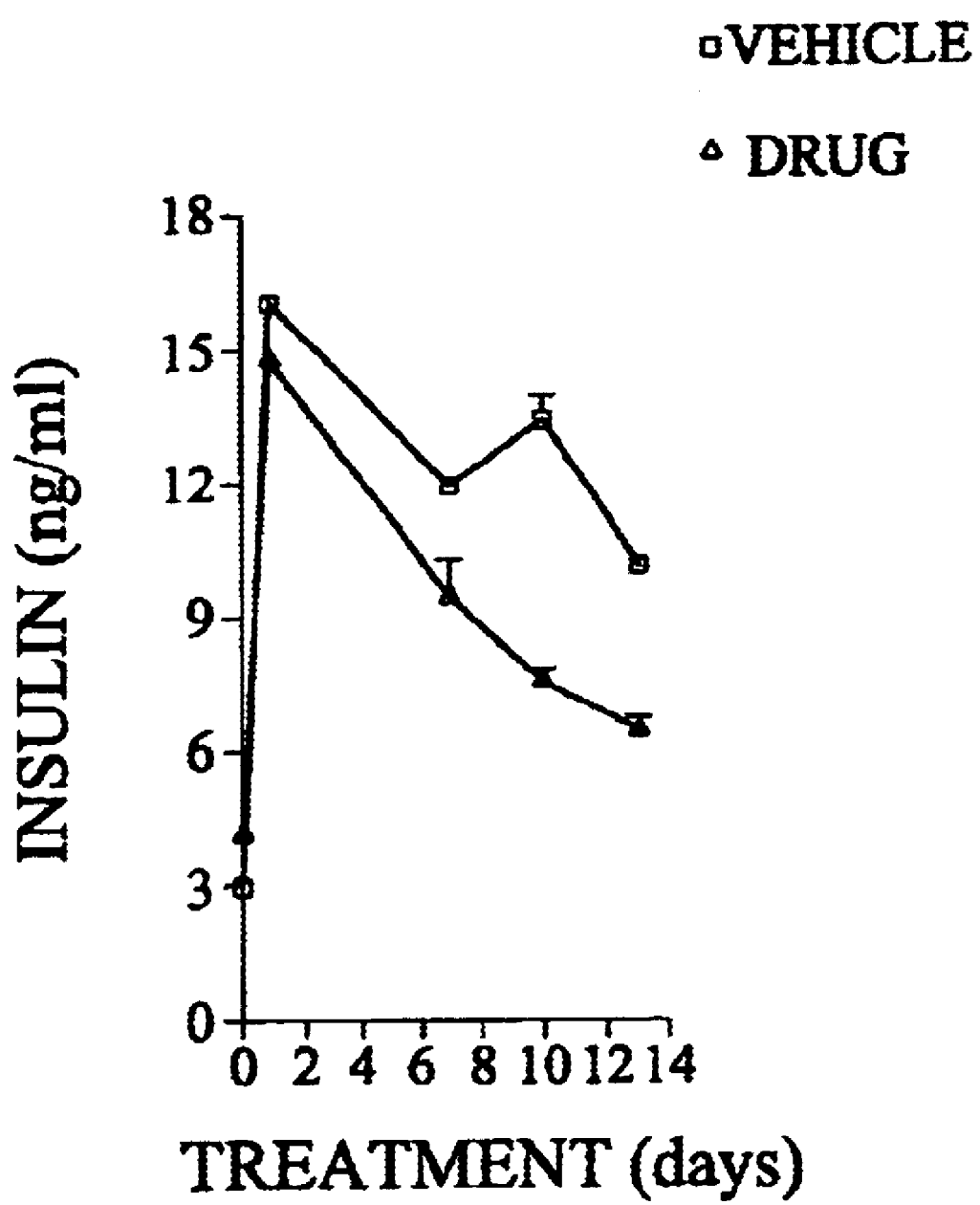
FIG. 4 shows the effect of the compound in Example 1 on glucose tolerance in Zucker rats.

Referring to FIG. 4, twelve obese hyperinsulinemic and insulin resistant Zucker (fa/fa) rats were randomized into groups designated as the test group and control group. Six of the test group were kept on the compound of Example 1 (20 mg/kg/BW/oral) once per day for a period of thirteen days. The control group was gavaged with an equal volume of PBS. Basal plasma insulin levels were monitored intermittently every three or four days during the course of the thirteen day study. The results in FIG. 4 show that the compound has an effect on lowering plasma insulin levels in this animal model.

EXAMPLE 10

Figure 5A:
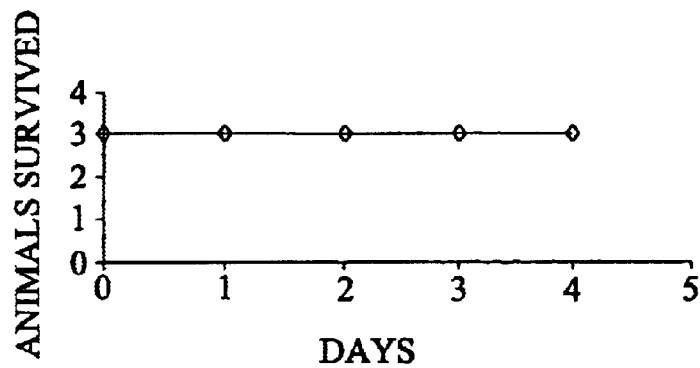
FIGS. 5A, 5 and 5C show, respectively, results of a lethal effect study on Swiss Webster mice by administration of dosages of 16.7, 167, and 333 mg/kg/BW on day zero.
Figure 5B:
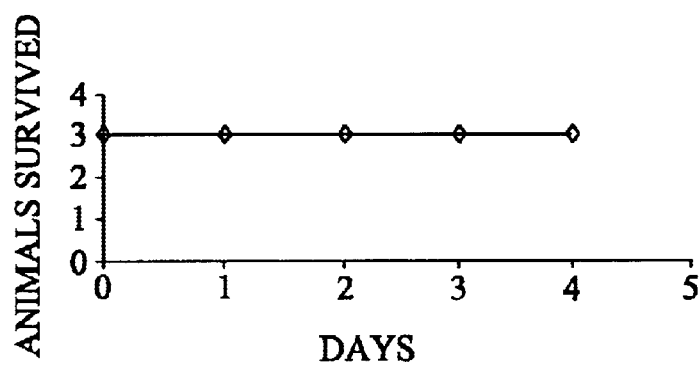
Figure 5C:
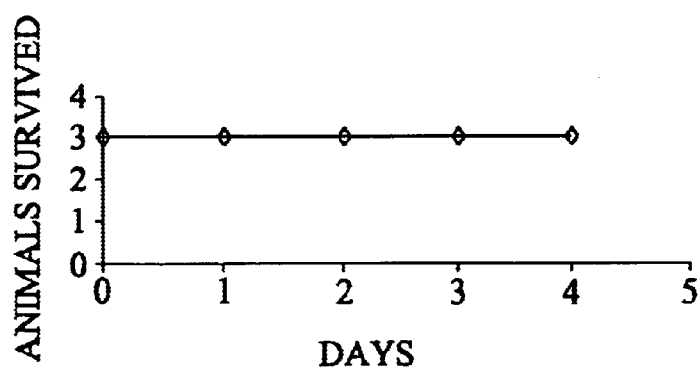

Nine healthy male Swiss Webster mice were divided into three study groups of three. The first study group (FIG. 5A) received the compound of Example 1 at a dose of 16.7 mg/kg/BW, the second study group (FIG. 5B) received a dose of 167 mg/kg/BW, and the third study group (FIG. SC) received a dose of 333 mg/kg/BW on day zero of the study. The mice were kept on regular food and water during the entire study period. During the study, the mice were under close observation and their behavior, gross physiology and mortality/survival were monitored. FIGS. 5A, 5B and 5C show that the survival rate in these mice in the course of the study period was 100%.

What is claimed is:

1. A pharmaceutical composition for the oral treatment of diabetes comprising a therapeutically effective amount of 2-(4-hydroxyphenyl)-3-(3, 5-dimethoxyphenyl) propenoate and a physiologically acceptable carrier, in a tablet or capsule containing binders or fillers suitable for oral administration.

2. A composition according to claim 1 which is the sodium propenoate.

3. A compositon according to claim 1 or 2 wherein said propenoate is in the E- configuration.

4. A composition according to claim 1 or 2 wherein said propenoate is in the Z- configuration.

5. A composition according to claim 1, wherein said composition is suitable for oral administration.

6. A method of treating diabetes comprising a step of administering to a subject suffering from a diabetic condition a therapeutically effective amount of 2-(4-hydroxyphenyl)-3-(3,5-dimethoxyphenyl)propenoate in a physiologically acceptable carrier.

7. A method according to claim 6 which is the sodium propenoate.

8. A method according to claim 6 or 7 wherein said propenoate is in the E- configuration.

9. A method according to claim 6 or 7 wherein said propenoate is in the Z- configuration.

10. A method according to claim 6, wherein said compound is orally administered to said subject.

11. A pharmaceutical composition for the oral treatment of diabetes comprising a therapeutically effective amount of a compound, or mixture of compounds of the formula:

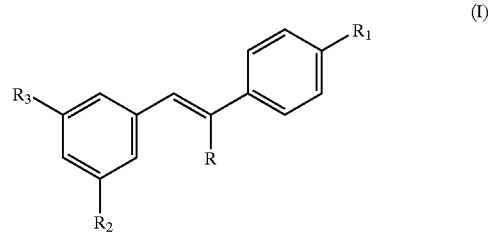

wherein R is hydrogen or —$CO_2Z$, Z is H or a cation; and
$R_1$, $R_2$, $R_3$, are each independently H, —OH, —$OR_4$ wherein $R_4$ is linear or branched alkyl of 1–12 carbon atoms;
with the proviso that when R is H and $R_2$=$R_3$=—OMe, then $R_1$ is not —OH; and
a physiological carrier, in a tablet or capsule containing binders or fillers suitable for oral administration.

12. The composition according to claim 11, wherein $R_2$ and $R_3$ are OMe.

13. The composition according to claim 12, wherein R is —$CO_2Z$ and $R_1$ is OH.

14. A composition according to claim 11 wherein said compound is in the E- configuration.

15. A composition according to claim 13 wherein said compound is in the E- configuration.

16. A composition according to claim 13 wherein said compound is in the Z- configuration.

17. The composition of claim 1, comprising compound Z-2-(4-hydroxyphenyl)-3-(3, 5-dimethoxyphenyl) propenoate.

18. The composition according to claim 17 wherein said compound is the sodium propionate.

* * * * *